(12) United States Patent
Kong et al.

(10) Patent No.: US 7,365,191 B2
(45) Date of Patent: Apr. 29, 2008

(54) TYPE OF OLIGOSACCHARIDES AND THEIR SULFATE DERIVATIVES

(75) Inventors: Fanzuo Kong, Haidian District (CN); Jun Ning, Haidian District (CN); Jianxin Gu, Shanghai (CN)

(73) Assignee: Shanghaimed Co., Ltd (CN)

( * ) Notice: Subject to any disclaimer, the term of this patent is extended or adjusted under 35 U.S.C. 154(b) by 393 days.

(21) Appl. No.: 10/482,977

(22) PCT Filed: Jul. 5, 2002

(86) PCT No.: PCT/CN02/00478

§ 371 (c)(1),
(2), (4) Date: Jan. 5, 2004

(87) PCT Pub. No.: WO03/004507

PCT Pub. Date: Jan. 16, 2003

(65) Prior Publication Data

US 2004/0197289 A1    Oct. 7, 2004

(30) Foreign Application Priority Data

Jul. 6, 2001    (CN) ................... 01 1 19997
Oct. 11, 2001    (CN) ................... 01 1 36237

(51) Int. Cl.
*A61K 31/702*    (2006.01)
*A61K 31/716*    (2006.01)
*C07H 3/06*    (2006.01)

(52) U.S. Cl. .................. 536/123.12; 536/123.1; 514/54; 514/61

(58) Field of Classification Search .............. 514/54; 536/102

See application file for complete search history.

(56) References Cited

U.S. PATENT DOCUMENTS 5,929,037 A * 7/1999 Srivastava et al. ............ 514/25

FOREIGN PATENT DOCUMENTS

| CN | 1242371 A | 1/2000 |
|----|-----------|--------|
| CN | 1303857 A | 7/2001 |
| CN | 1332177 A | 1/2002 |
| CN | 1336387 A | 2/2002 |

OTHER PUBLICATIONS

Moothoo, D. et al "Concanavalin A distorts the beta-GlcNAc ... " Glycobiology (1998) vol. 8, No. 2, 173-181.*
Hirooka et al., "Dehydrative Glycosylation by Diethylaminosulfur Trifluoride (DAST)-Tin(II) Trifluoromethanesulfonate-Tetrabutylammonium Perchlorate-Triethylamine System" Bull. Chem. Soc. Japan, (1998) vol. 71, pp. 2893-2902.*
Koto et al. "Dehydrative Glycosylation Using Heptabenzyl Derivatives of GLucobioses and Latose" Bull. CHem. Soc. Jpn. (1992) vol. 65, pp. 3257-3274.*

* cited by examiner

*Primary Examiner*—Shaojia Anna Jiang
*Assistant Examiner*—Eric S Olson
(74) *Attorney, Agent, or Firm*—McDonnell Boehnen Hulbert & Berghoff LLP

(57) ABSTRACT

This invention involves a type of oligosacoharides and its their sulfate derivatives. The backbone of the oligosaccharides consists of 4 to 14 glucose residues, while the side chains contain 0 to 4 glucose residues. There are at least one 1->3α linkage and β-(1->3)-linkage or β-(1->4) linkage in the backbone. These oligosaccharides, and their sulfates have immune enhancing, antitumor, and antiviral activities. They can be used in immune enhancing, antitumor, and antiviral medicine compounds that would be used as therapeutic treatments.

15 Claims, No Drawings

TYPE OF OLIGOSACCHARIDES AND THEIR SULFATE DERIVATIVES

This application is a national stage application of PCT/CN02/00478, filed Jul. 5, 2002, which claims priority to foreign applications CN01119997.0, filed Jul. 6, 2001 and CN01136237.5, filed Oct. 11, 2001.

TECHNICAL FIELD

This invention describes a type of oligosaccharides and its sulfate derivatives, being capable of medicinal uses. This invention further describes dendrimers of these oligosaccharides linked by polyhydroxyl compounds. Also, This invention describes the use of the said oligosaccharides, their sulfate derivatives, and dendrimers that can be used as antitumor, immune enhancing, and anti-infectious medicine.

BACKGROUND OF THE TECHNIQUE

It has been known, up to now, that carbohydrates with antitumor activity are mostly polysaccharides such as lentinan, schizophyllan, and sceroglucan, obtainable from edible fungi or from Chinese traditional herbs. There have been rare reports dealing with the oligosaccharides with immune-enhancing and antitumor activity. An oligosaccahride, α-L-Fuc-(1-2)-β-D-Gal-(1-3)-β-D-GalNAc-(1-3)-α-D-Gal-(1-4)-β-Gal-(1-4)-D-Glu, a hexasaccharide consisting of fucose, galactose, N-acetyl-galactose, and glucose (*J. Am. Chem. Soc.* 1995, 117, 7840) can be used as an antigen against breast cancer and now is in clinical trials. Lentinan has been shown to have antitumor and immune-enhancing activity. Lentinan does not directly attack the tumor cells, but stimulates the host immune system to destroy the tumor cells. In our previous patent (Jun Ning, Fanzuo Kong, application number of Chinese Patents: 99126224.7), synthesis of core fragments of lentinan was reported. These fragments consisted of β-linkages showing immune-enhancing and antitumor activities (Jun Ning, Fanzuo Kong, application number of Chinese Patents: 00100376.3). Sulfation of branched oligosaccharides can give them additional properties such as anti-inflammatory and anti-infectious etc. There have been reports dealing with anti-inflammation and inhibition of cell metastasis (WO96/33726).

The repeating heptaose unit of lentinan has the following structure:

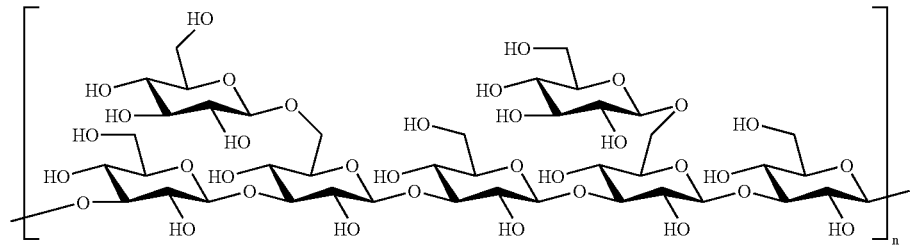

It is seen from the above structure that all of the linkages in the heptaose are β-linkages.

Different oligosaccharide structures are related to corresponding antigens of different diseases. Synthesis of certain oligosaccharides by known methods is a complex process. Thus far, there have been no reports dealing with the synthesis and use of the heptaose analogues containing α-linkeges.

OPEN OF THE INVENTION

The main goal of the invention is to generate a type of oligosaccharides and its sulfate derivatives;

The $2^{nd}$ goal of the invention is to generate a type of dendrimers of the said oligosaccharides linked by polyhydroxyl compounds;

The $3^{rd}$ goal of the invention is to generate a type of medicinal ingredients that have immune enhancing, antitumor or anticancer properties.

This invention describes a type of oligosaccharides and its sulfate derivatives. The oligosaccharides are presented in the following formula [I]:

In the formula,

[Rx]n=backbone of the said oligosaccharides, Rx=sugar residue, and n=integral of 3 to 14;

$R_1$=side chain of the said oligosaccharides, $R_1$=monosaccharide or oligosaccharide, $R_1$ are composed of the same or different sugar residue; m=number of side chains, being an integer from 0 to 4;

$R_2$ and $R_3$=nonreducing and reducing end respectively. When $R_2$ and $R_3$=H, the said oligosaccharides are free oligosaccharides. When $R_2$=H and $R_3$=C1-20 hydrocarbon group; the said oligosaccharides are glycosides;

The backbone of the said oligosaccharides has at least one α-(1→3)-linkage, and the said side chain $R_1$ is attached to the backbone with a β-(1→6)- or an α-(1→6)-linkage.

The backbone of the said oligosaccharides predominantly have β-(1→3)-linkages or β-(1→4)-linkages.

The said oligosaccharides have characteristic side chains $R_1$ which are closely or separately positioned.

The said oligosaccharides have characteristic side chains $R_1$ which are separated by one sugar residue of the backbone or by more than 2 sugar residues of the backbone.

The degree of hydroxyls sulfation of the said oligosaccharides is more than 0.2.

The preferred degree of hydroxyls sulfation of the said oligosaccharides is 0.33 to 0.67.

The said oligosaccharides in formula [I] have a backbone with Rx=glucose, galactose or mannose. The said oligosaccharides in formula [I] have a preferred backbone with Rx=glucose. The said oligosaccharides in formula [I] have a preferred structure with the backbone Rx=glucose, and the side chains R1=glucose.

The said oligosaccharides in formula [I] are preferred to be tetrasaccharide, pentasaccharide, hexasaccharide or heptasaccharide. Rx of the said oligosaccharides backbone is preferred to be glucose, galactose, or mannose. The preferred tetrasaccharide includes β-Glc-1→3-α-Glc-1→3-β-Glc-1→3-Gluc, or α-Man-1→3-α-Glc-1→3-β-Glc-1→3-Gluc. The preferred pentasaccharide includes β-Glc-1→3-α-Glc-1→3-β-Glc-1→3-β-Glc-1→3-Glc, or β-Glc-1→3-α-Glc-1→3-β-Glc-1→3-α-Glc-1→3-Glc.

The preferred hexasaccharide includes the following formula 18, 18', or 18".

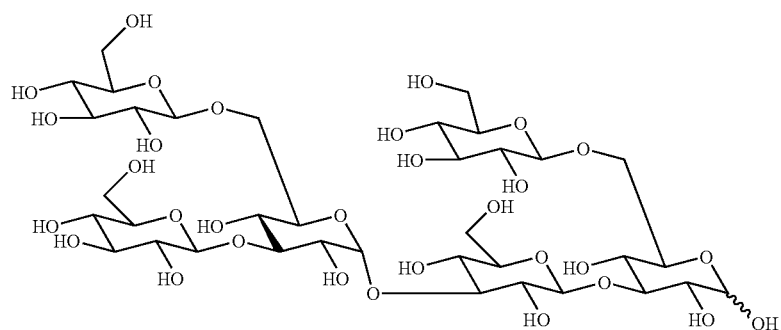

18

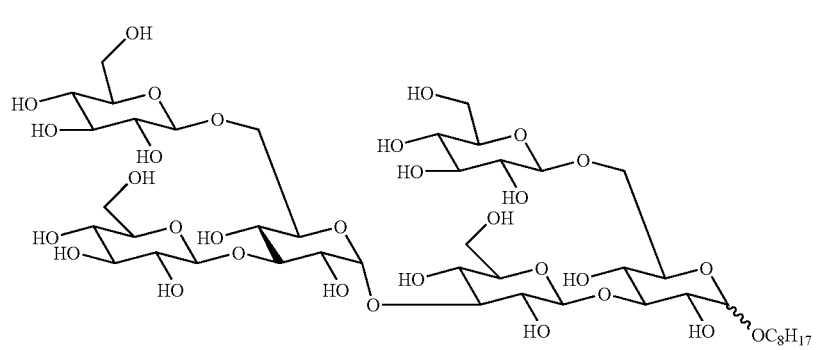

18'

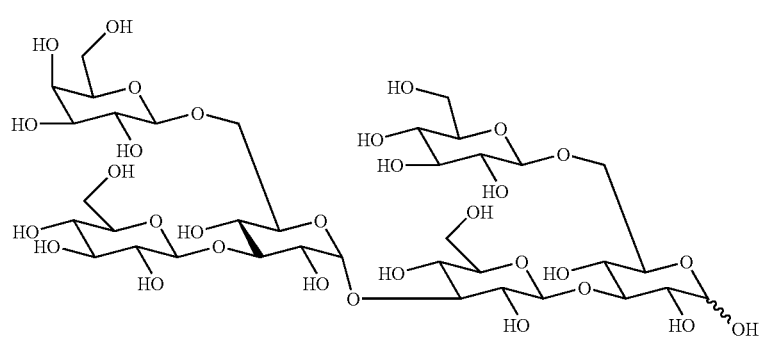

18"

The preferred heptasaccharide includes the following formula 24:

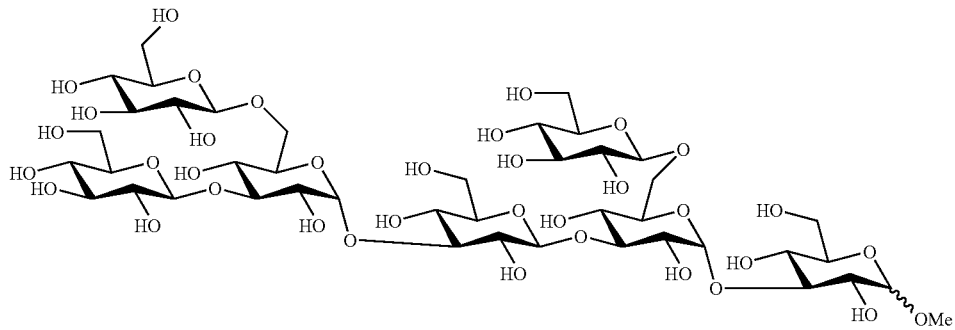

24

The invention also describes a type of oligosaccharide dendrimers linked by polyhydroxyl compounds with the following formula [II]

[II]

In the formula, [Z]p represents a carbon chain, Z represents CH in the presence of a side chain, or $CH_2$ group in the absence of a side chain.

(OY)q represents a side chain, q is an integer of either 2 or 3, Y represents oligosaccharides with the following formula:

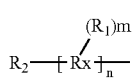

[III]

In the formula, [Rx]n=the backbone of the said oligosaccharides, Rx=sugar residues, which can be the same sugar residue or different, and n=number of sugar residues, being an integer from 3 to 14;

$R_1$=side chain of the said oligosaccharides, $R_1$=monosaccharide or oligosaccharide, $R_1$ are composed of the same or different sugar residue; m=number of side chains, being an integer of 0 to 4;

$R_2$=H, representing nonreducing end;

The backbone of the said oligosaccharides has at least one α-(1→3)-linkage, and the said side chain $R_1$ is attached to the backbone with a β-(1→6)- or an α-(1→6)-linkage;

Y is linked with the said oligosaccharides by an O-glycosyl bond.

As described in formula [II] regarding the oligosaccharide dendrimers linked by polyhydroxyl compounds, the preferred number q is 2 or 3, with 2 being the preferred number.

The said oligosaccharide dendrimers have the preferred sugar residue Rx=glucose, galactose, or mannose.

The said oligosaccharide dendrimers have the preferred Y being either a trisaccharide up to heptasaccharide inclusive. The preferred hexasaccharide dendrimer has the following formula 17:

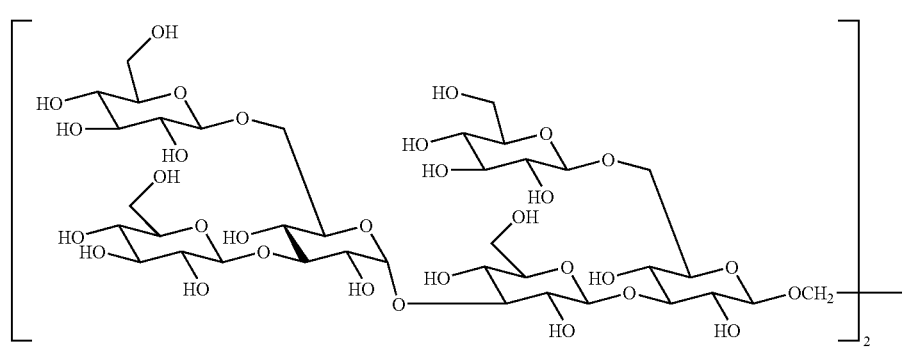

17

The invention also involves the uses of the said oligosaccharides, their sulfate derivatives, and their dendrimers. They can be used in antitumor, anticancer, and immune enhancing medicinal compounds. Furthermore, the sulfate derivatives of the said oligosaccharides can be used in anti-inflammatory and anti-infectious medicinal compounds. These compounds in effective dosage with their diluted solutions or in a preparation with carriers can effectively inhibit tumorigenesis and inflammation, and can also significantly boost immunological function.

THE BEST WAY TO REALIZE THE INVENTION

The following examples are used to illustrate the invention, but they can not limit the invention.

EXAMPLE 1

Preparation of the Trisaccharide Donor and Trisaccharide Acceptor (1) Preparation of the trisaccharide donor 9:

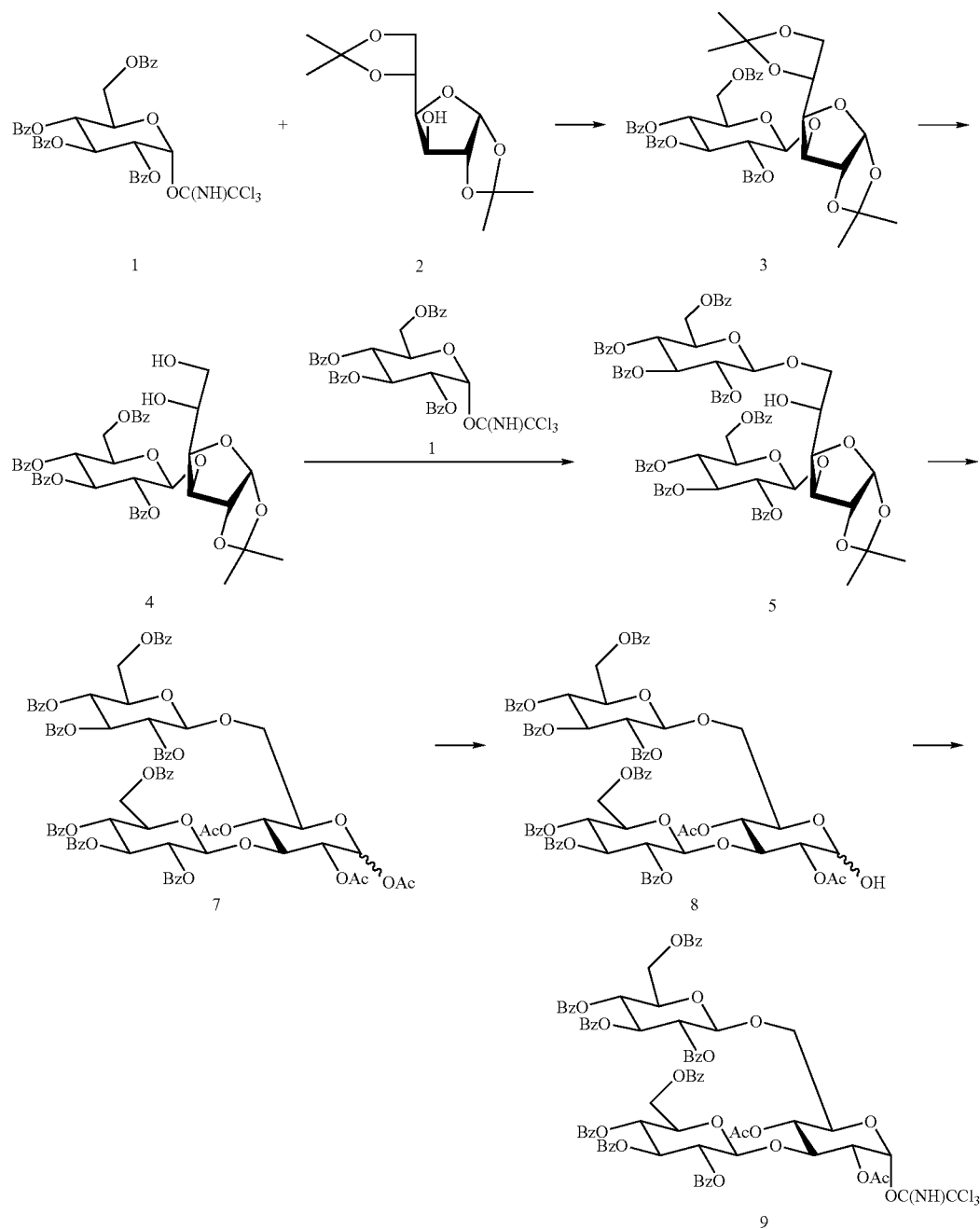

2,3,4,6-Tetra-O-benzoyl-α-D-glucopyranosyl trichloroacetimidate (1, 5.6 g, 7.56 mmol) was dissolved in dichloromethane (40 mL), giving solution A, and 1,2:5,6-di-O-isopropylidene-D-glucose 2 (2.8 g, 10.77 mmol) was dissolved in dichloromethane (20 mL), giving solution B. Then solution A was combined with solution B, to generate solution C. Then TMSOTf (0.08 mmol) was added to solution C. After stirring the mixture for 2 h at room temperature, TLC analysis indicated that the reaction was complete. The reaction mixture was diluted with dichloromethane (100 mL), then 0.5% HCl/MeOH (200 mL) was added. After stirring the mixture for 1 h at room temperature, the 5,6-O-isopropylidene was selectively removed. The mixture was neutralized with triethyl amine, and concentrated to dryness under reduced pressure. The residue was purified by silica gel chromatography with petroleum ether-EtOAc (2/1) as the eluent gave the disaccharide 4 (5.43 g, 90%).

The donor 1 (3.7 g, 5.01 mmol) was dissolved in dichloromethane (30 mL), giving solution A. and the disaccharide acceptor 4 (4.0 g, 5.01 mmol) was dissolved in dichloromethane (30 mL), creating solution B. Then solution A was combined with solution B, to generate solution C. Then TMSOTf (0.05 mmol) was added to solution C. After stirring the mixture for 3 h at room temperature, TLC analysis indicated that the reaction was complete. The reaction mixture was neutralized with triethylamine, and washed with water. The aqueous phase was discarded and the organic phase was concentrated. The residue was purified by silica gel chromatography with petroleum ether-EtOAc (1/1) as the eluent gave the trisaccharide 5 (5.86 g).

The trisaccharide 5 (6.0 g, 4.36 mmol) was dissolved in 80% aqueous HOAc (50 mL), and the mixture was heated at 60° C. until TLC analysis indicated completion of the reaction. Concentration of the reaction mixture to dryness was performed, and the residue was acetylated with acetic anhydride in pyridine to give trisaccharide 7.

The trisaccharide 7 (5.5 g, 3.76 mmol) was dissolved in DMF (30 mL), and $NH_4HCO_3$ (3 g) was added. The reaction was carried out at room temperature and monitored by TLC analysis. After completion of the reaction, the mixture was concentrated, and the residue was dissolved in dichloromethane (40 mL). To the solution, $CCl_3CN$ (3 mL) and $K_2CO_3$ (3 g) were added. The reaction mixture was stirred at room temperature overnight. TLC analysis indicated that the reaction was complete. The reaction was worked up using conventional method, and the product was purified by silica gel chromatography with petroleum ether-EtOAc (1/1) as the eluent to give the trisaccharide donor 9 (6.01 g, 91%). $[\alpha]_D$+23.3° (c 1.0, $CHCl_3$); $^1H$ NMR (400 MHz, $CDCl_3$): δ 8.33 (s, 1 H, $CNHCCl_3$), 8.07-7.19 (m, 40 H, 8 PhH), 6.19 (d, 1 H, J 3.6 Hz), 5.91 (dd, 1 H, J 9.6 Hz), 5.85 (dd, 1 H, J 9.6 Hz), 5.62 (dd, 1 H, J 9.6 Hz), 5.61 (dd, 1 H, J 9.6 Hz), 5.46 (dd, 1 H, J 7.9, 9.6 Hz), 5.42 (dd, 1 H, J 7.9, 9.6 Hz), 4.97 (d, 1 H, J 7.9 Hz), 4.96 (d, 1 H, J 7.9 Hz), 4.85 (dd, 1 H, J 9.5 Hz), 4.67-4.59 (m, 3 H), 4.50-4.37 (m, 2 H), 4.19-4.02 (m, 4 H), 3.91(dd, 1 H), 3.69 (dd, 1 H), 1.94, 1.78 (2 s, 6 H, 2 $CH_3CO$); Anal. Calcd for $C_{80}H_{68}Cl_3NO_{26}$: C, 61.37; H, 4.38. Found: C, 61.53; H, 4.41.

(2) Preparation of trisaccahride acceptor 14:

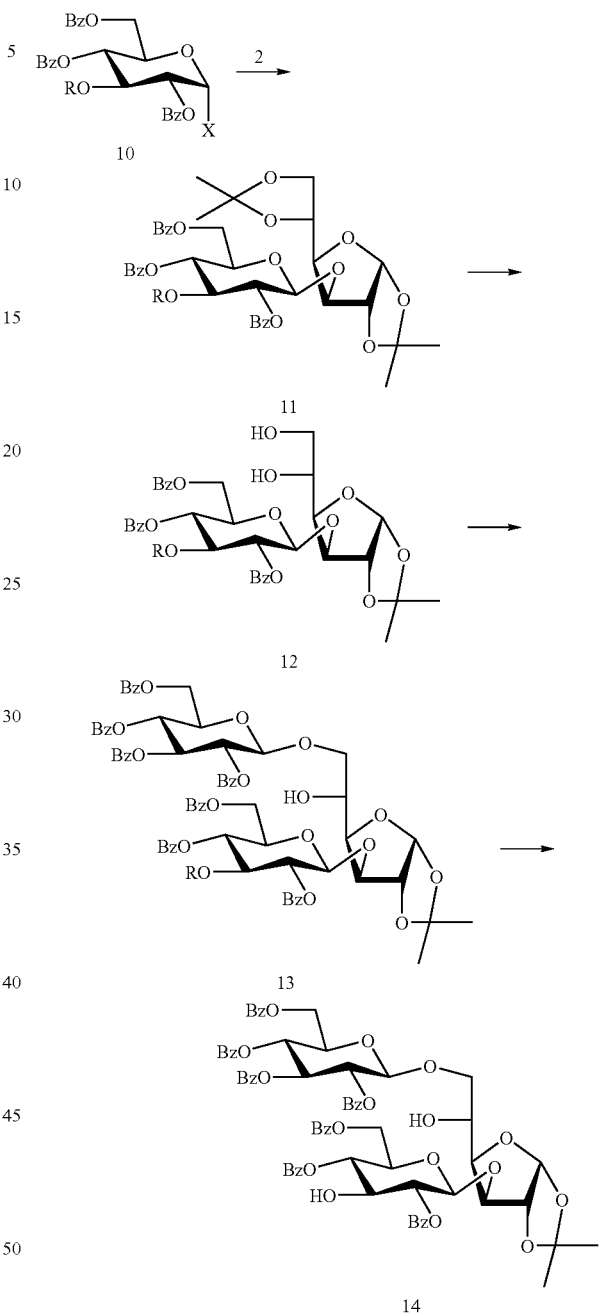

X=trichloroacetimidate

Coupling of 3-O-allyl-2,4,6-tri-O-benzoyl-α-D-glucopyranosyl trichloroacetimidate 10 (4.10 g, 8.38 mmol) with the acceptor 2 (2.13 g, 8.20 mmol) under the same conditions as used for coupling of 1 with 2. After completion of the reaction, the reaction mixture was diluted with dichloromethane (100 mL) and 0.5% HCl/$CH_3OH$. After stirring the mixture for 1 h, the 5,6-O-isopropylidene group was selectively removed. The reaction mixture was neutralized with triethylamine, and concentrated under reduced pressure. The residue was purified by silica gel chromatography with petroleum ether-EtOAc (1/1) as the eluent to give the disaccharide 12 (4.12 g, 88%). Then Coupling of 12 with 1, under the same conditions as described for the coupling of 1 with 2, gave the trisaccharide 13 (5.07 g, 64%). After acetylation of 13 with acetic anhydride in pyridine, the trisaccharide was dissolved in MeOH (100 mL), and PdCl$_2$ (0.5 g) was added. The reaction was carried out at room temperature and monitored by TLC analysis. After completion of the reaction, the mixture was filtered, and the filtrate was concentrated to dryness. Purification by silica gel chromatography with petroleum ether-EtOAc (1/1) as the eluent gave the trisaccharide acceptor 14 (4.22 g, 87%). [α]$_D^{25}$- 15°(c 1.0, CHCl$_3$); $^1$HNMR (CDCl$_3$, 400 MHz): β 8.16-7.25(m, 20H, Bz-H), 6.14(t, 1H, J10.18 Hz,), 5.89-5.85(m, 2H), 5.77-5.75 (m, 1H), 5.29(d, 1H, J8.72 Hz), 5.10(s, 1H, H-1), 4.97-4.93 (t, 1H, J9.55 Hz), 4.87-4.82 (t, 1H, J9.46 Hz), 4.80-4.71 (m, 2H), 4.66-4.62 (m, 1H), 4.58 (d, 1H, J7.91 Hz), 4.57-4.48 (m, 2H), 4.39 (d, 1H, J5.15 Hz), 4.28-4.19 (m, 1H), 4.18-4.06 (m, 2H), 3.93-3.85 (d, 1H, J10.8 Hz), 3.71 (t, 1H, J9.46 Hz), 3.68-3.56 (m, 1H), 2.12, 2.10, 2.10, 2.09 (s, 12H, 4CH$_3$C═O) 1.55 1.33 (s, 6H, 2CH$_3$C═O).

EXAMPLE 2

Preparation of hexasaccharide (1) Preparation of the hexasaccharide 18 consisting of only glucose:

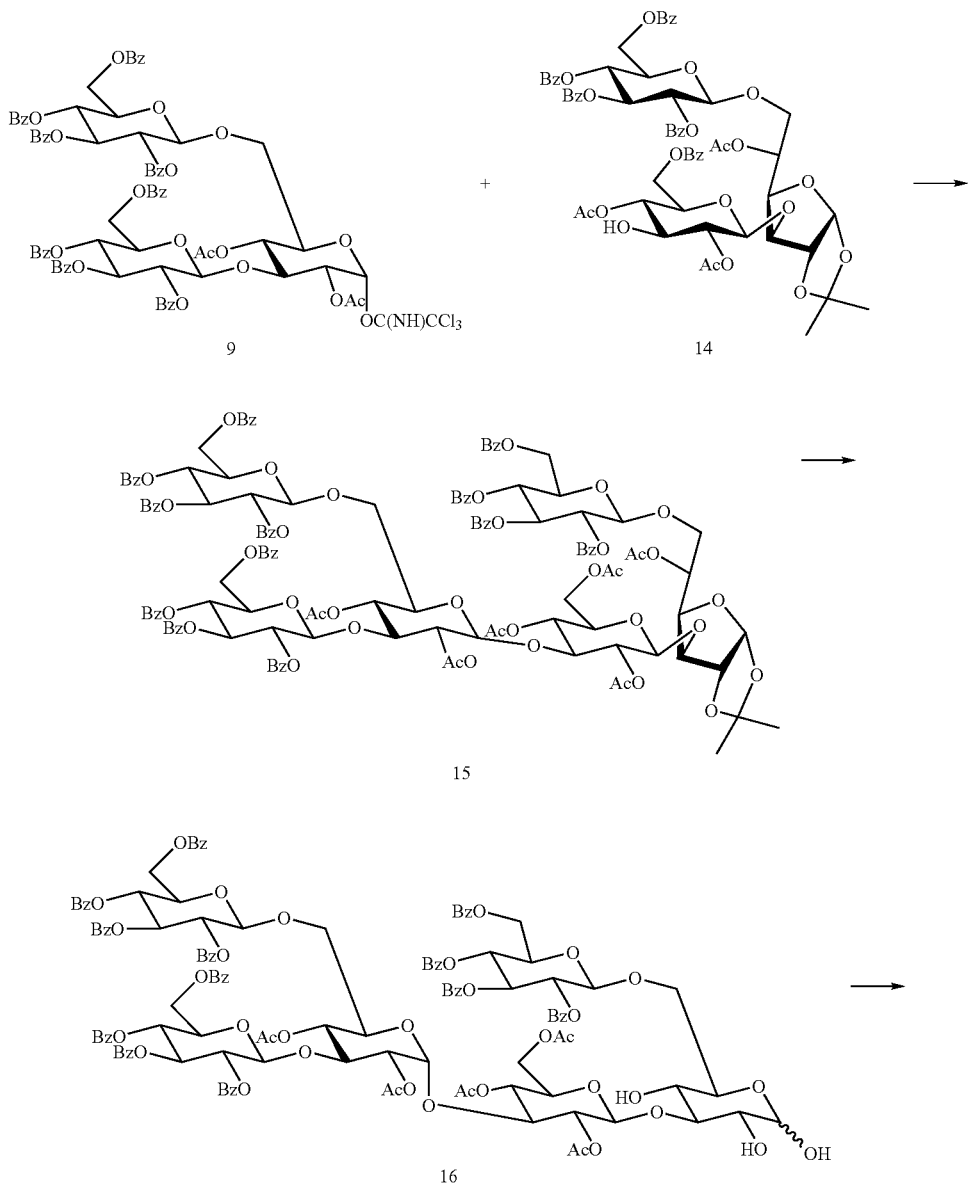

-continued

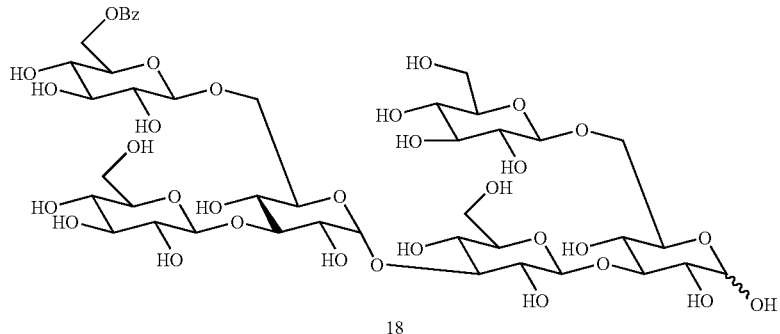

18

The trisaccharide donor 9 (3 g, 1.92 mmol) and the trisaccharide acceptor 14 (2.12 g, 1.92 mmol) were dissolved in dichloromethane (40 mL). The solution was cooled with an ice-salt bath, to the solution was added TMSOTf (0.02 mmol), and the mixture was gradually warmed to ambient temperature. The reaction was carried out under nitrogen protection with stirring, and monitored by TLC analysis. After completion of the reaction, the mixture was worked up using conventional method. Purification of the product by column chromatography on silica gel with petroleum ether-EtOAc (1/2) as the eluent gave the hexasaccharide 15 (4.11 g, 80%). Subsequent hydrolysis of 15 (3.5 g, 1.31 mmol) in 80% aqueous HOAc (40 mL) at 60° C. was monitored by TLC. After completion of the reaction, the mixture was concentrated under reduced pressure. Purification of the product by column chromatography on silica gel with petroleum ether-EtOAc (1/2) as the eluent gave the product. Acetylation of the crude product with acetic anhydride in pyridine quantitatively gave peracylated hexasaccharide (3.25 g, 90%). Subsequent deacylation (2 g, 0.72 mmol) in ammonia-saturated methanol (40 mL) was carried out overnight and monitored by TLC analysis. After completion of the reaction, the mixture was concentrated and washed with dichloromethane to give powdered 18 (681 mg, 95%). $[\alpha]_D^{25}$ +24°(c 1.0, CHCl$_3$); $^1$HNMR (CDCl$_3$, 400 MHz): δ 5.24(d, 2H), 4.89 (s, 1H), 4.57 (s, 1H), 4.50 (d, 1H, J7.9 Hz), 4.12-3.44 (m, 38H); $^{13}$C NMR δ 105.27, 102.66, 100.34, 96.42 (C-1$^{I-VI}$ some signals overlapped), 83.54, 79.59, 78.38, 76.68, 75.36, 74.23, 72.37, 71.44, 70.73, 69.98, 69.86, 69.69, 69.43, 69.27, 66.20, 66.09, 60.78, 60.31 (C-2, 3, 4, 5, 6$^{I-VI}$, some signals overlapped).

(2) Preparation of hexasaccharide 18″ containing galactose

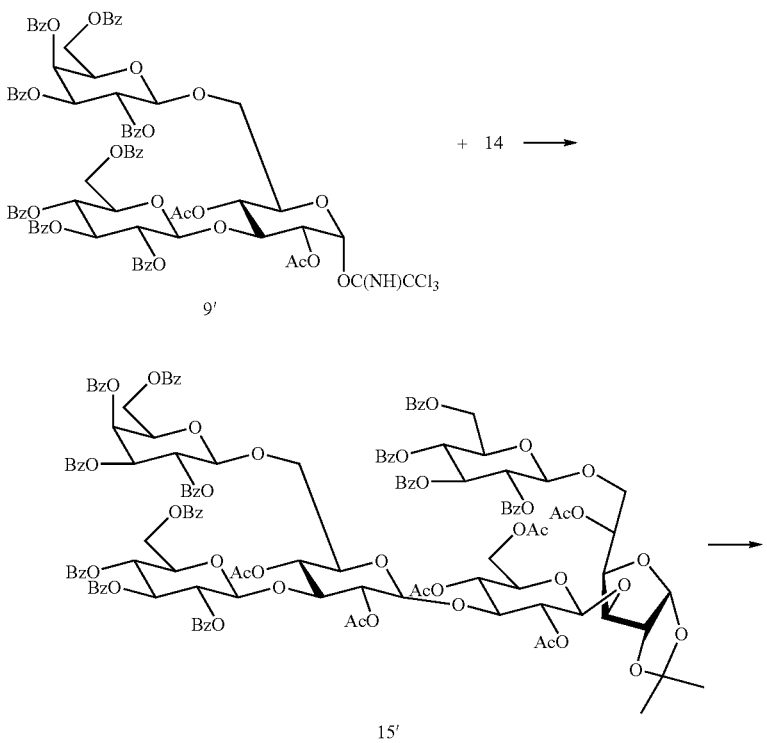

-continued

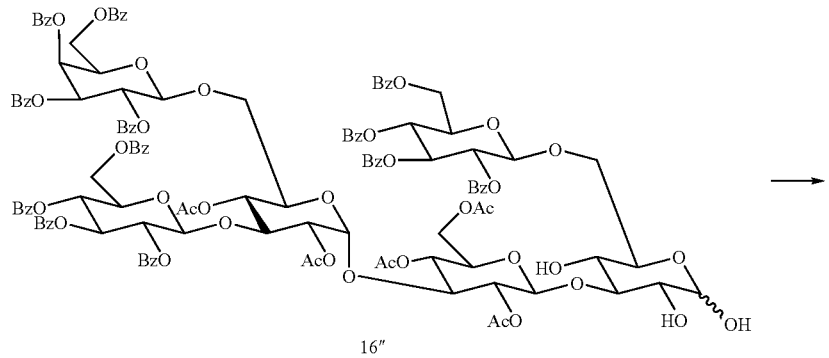

16″

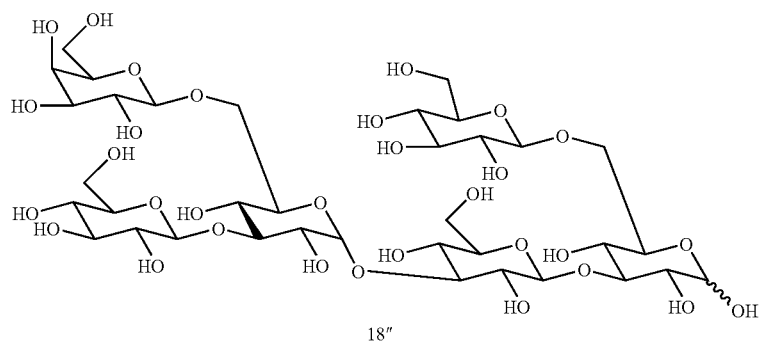

18″

According to the preparation of hexasaccharide 18 by coupling of the trisaccharide 9 with the trisaccharide 14, condensation of trisaccharide 9' (2.4 g) with the trisaccharide 14 (1.7 g) gave the hexasaccharide 18″ (560 mg) through the same procedure. $[\alpha]_D^{25}$ +16° (c 1.0, CHCl$_3$); $^1$H NMR (CDCl$_3$, 400 MHz): δ 5.18 (d, 2H), 4.89 (s, 3H), 4.68 (s, 1H), 4.05-3.53 (m, 37H); $^{13}$C NMR δ 106.11, 104.43, 101.74, 99.32, 96.29 (C-1$^{I-VI}$ some signals overlapped), 87.65, 84.57, 79.98, 78.62, 76.57, 74.67, 73.54, 71.21, 70.87, 69.98, 69.65, 69.31, 69.00, 68.96, 66.20, 66.00, 59.78, 58.92, 58.12 (C-2, 3, 4, 5, 6$^{I-VI}$, some signals overlapped).

EXAMPLE 3

Preparation of Heptasaccharide (1) Preparation of the tetrasaccharide acceptor 22:

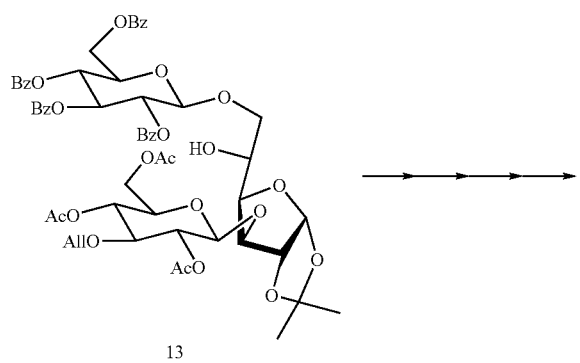

13

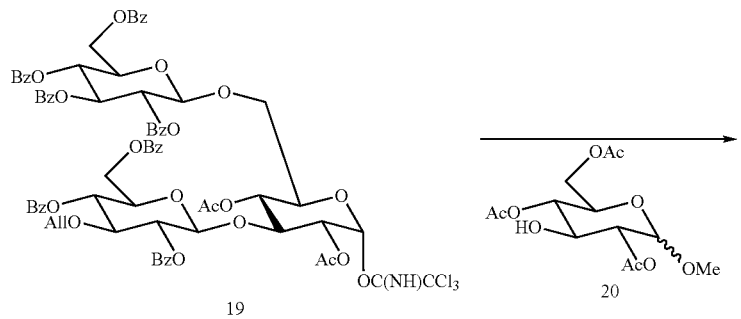

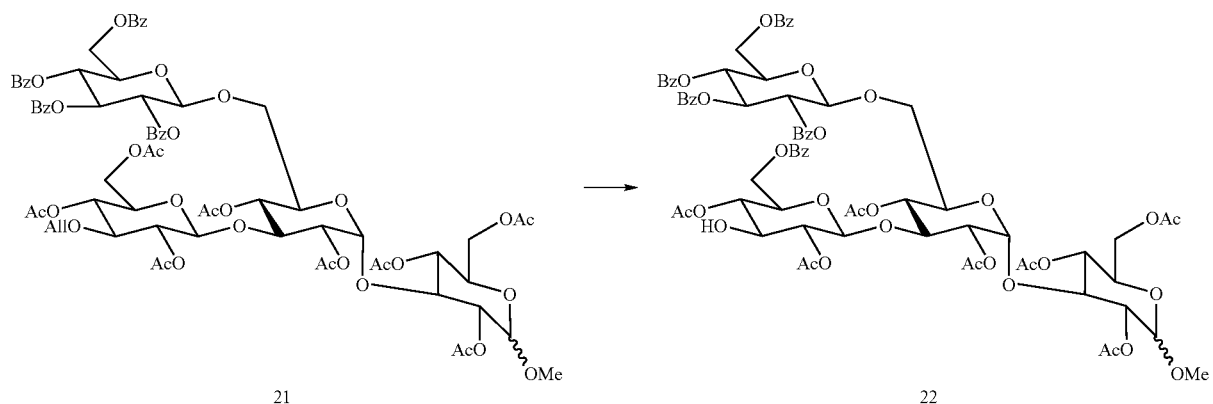

Under the same conditions as described for the preparation of trisaccharide donor 9 from trisaccharide 5, trisaccharide 13 was transformed to trisaccharide donor 19. Then the donor 19 (3.12 g, 2.13 mmol) was coupled with monosaccharide acceptor 20 (0.80 g, 2.50 mmol), under the same conditions as described for the coupling of 1 with 2, to give tetrasaccharide 21 (2.34 g, 69%). According to the procedure for preparation of 14 from 13, 21 was transformed to the tetrasaccharide acceptor 22.

(2) Preparation of the heptasaccharide 24:

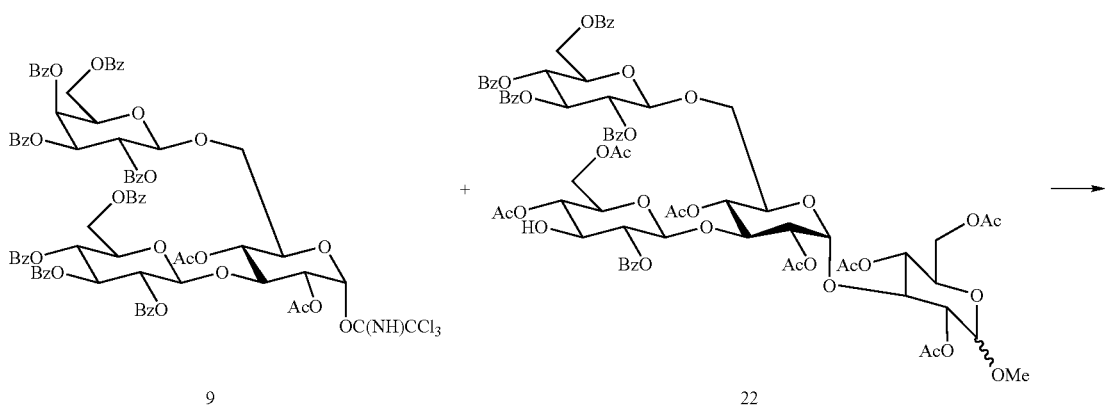

-continued
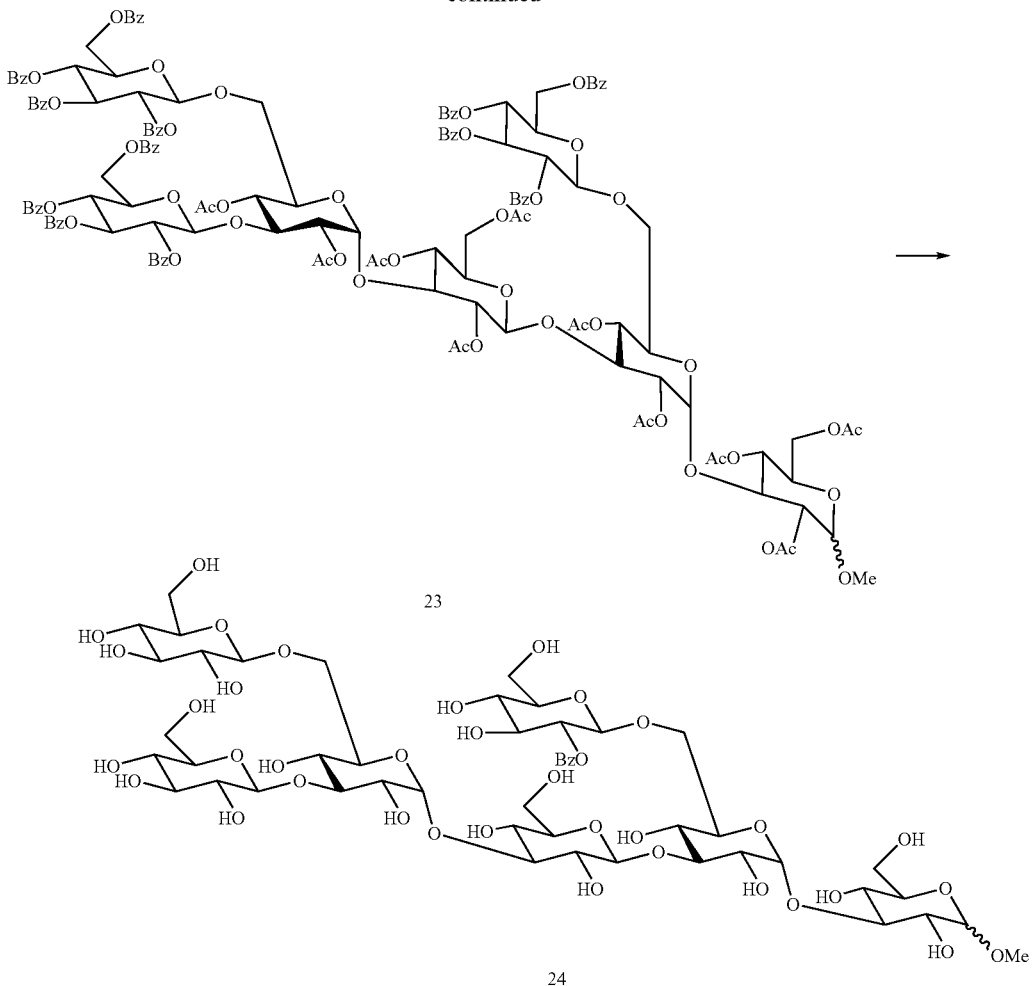
Coupling of 9 (2.30 g, 1.4 mmol) with 22 (2.26 g, 1.45 mmol), under the same conditions as used for coupling of 9 with 14 to give 18, created the heptasaccharide 23 (3.02 g, 70%). Deprotection gave the lentinan repeating heptaose unit 24. $[\alpha]_D$ –25.0° (c 0.1, $H_2O$); $^{13}C$ NMR (100 MHz, $D_2O$): δ 102.7, 102.6, 102.6, 102.4, 102.4, 102.1, 96.1(7 C-1), 56.1; ESMS for $C_{43}H_{74}O_{36}$ (1167.01): 1166.00 $[M-1]^+$.
EXAMPLE 4
Preparation of Octyl Hexaoside 18'
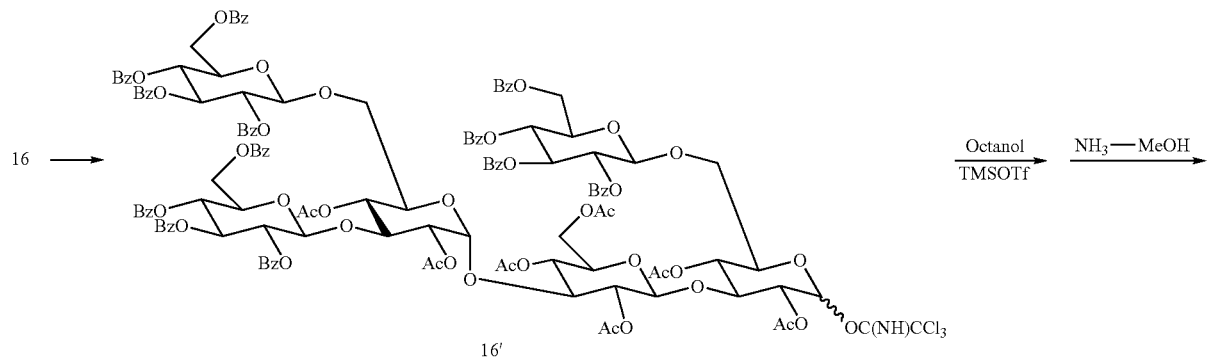

-continued

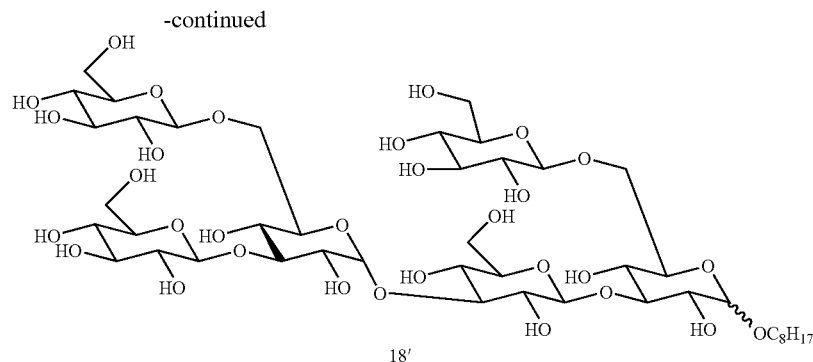

18'

To a solution of hexasaccharide 16 (2.34 g, 1 mmol) in dichloromethane (20 mL) were added trichloroacetonitrile (3 mL) and potassium carbonate (3 g). The reaction mixture was stirred for 23 h, and TLC analysis indicated that the reaction was complete. The reaction was worked up using conventional method, and the crude product was purified by column chromatography on silica gel with petroleum ether-EtOAc (1/1) as the eluent to give hexasaccharide donor 16' (81%). The hexasaccharide donor 16' was dissolved in dichloromethane (10 mL), then octyl alcohol (240 mg) and TMSOTf (15 µL) was added. The reaction was carried out at room temperature for 2 h, and TLC indicated that the reaction was complete. The reaction mixture was concentrated, and the residue was purified by column chromatography on silica gel with petroleum ether-EtOAc (2/1) as the eluent to give protected octyl glycoside of the hexasaccharide (1.82 g, 80%). The octyl glycoside was dissolved in ammonia-saturated methanol, and the reaction was carried out at room temperature for 7 days. Evaporation of the solvent, and the residue was washed with ethyl acetate to create white powdered octyl hexaoside 18' (645 mg, 95%). $[\alpha]_D$ -39.1° (c 0.2, $H_2O$); $^{13}C$ NMR (100 MHz, $D_2O$): δ 102.6, 102.5, 102.4, 102.4, 102.3, 96.3 (6 C-1), 84.0, 83.9 (2 C-3).

If pentenyl alcohol ($CH_2$=CH—$CH_2$—$CH_2$—$CH_2$—OH) was used in the above described reaction, pentenyl hexaoside of 18 was obtained: $[\alpha]_D$ -42.1° (c 0.3, $H_2O$); $^{13}C$ NMR (100 MHz, $D_2O$): δ 118.1, 117.2, 102.8, 102.6, 102.1, 102.0, 101.9, 96.5 (6 C-1), 84.2, 83.9 (2 C-3). ESMS for $C_{41}H_{70}O_{31}$ (1058.56): 1057.70 [M−1]$^+$.

If propynyl alcohol (CH≡CH—$CH_2$—OH) was used in the above described reaction, propynyl hexaoside of 18 was obtained: $[\alpha]_D$ -37.1° (c 0.3, $H_2O$); $^{13}C$ NMR (100 MHz, $D_2O$): δ 102.5, 102.3, 102.1, 102.0, 101.8, 96.2 (6 C-1), 84.2, 83.9 (2 C-3). ESMS for $C_{39}H_{64}O_{31}$ (1028.96): 1027.80 [M−1]$^+$.

EXAMPLE 5

Preparation of 17, the Dimer of the Hexasaccharide Linked by Glycol

To a solution of the hexasaccharide donor 16' (2.39 g, 1 mmol) and ethylene glycol (124 mg, 2 mmol) in dry dichloromethane (30 mL) was added TMSOTf (30 µL). The reaction was carried out at room temperature for 2 h, and TLC analysis indicated that the reaction was complete. The reaction mixture was concentrated, and the residue was purified by column chromatography on silica gel with petroleum ether-EtOAc (2/1) as the eluent to give the hexasaccharide dimer linked by glycol (3.6 g, 69%). The dimer was dissolved in ammonia-saturated methanol, and the reaction was carried out at room temperature for 7 days. Evaporation of the solvent, and the residue was washed with ethyl acetate to create white powdered dendrimer 17 (1.28 g, 91%).

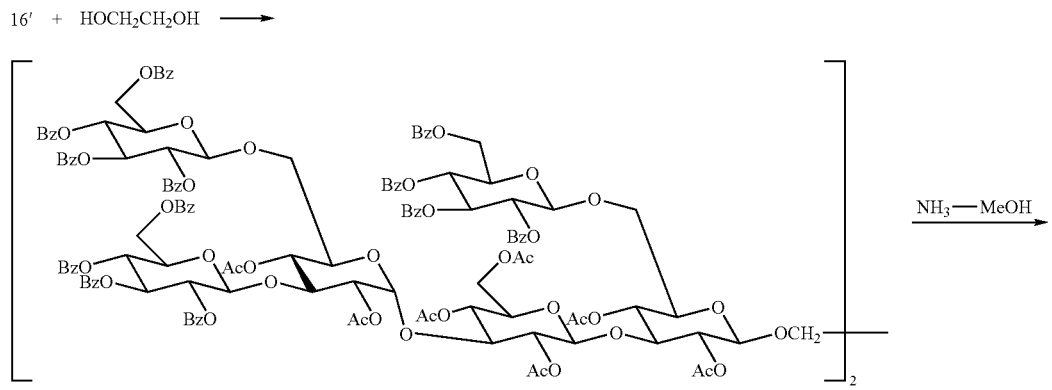

-continued

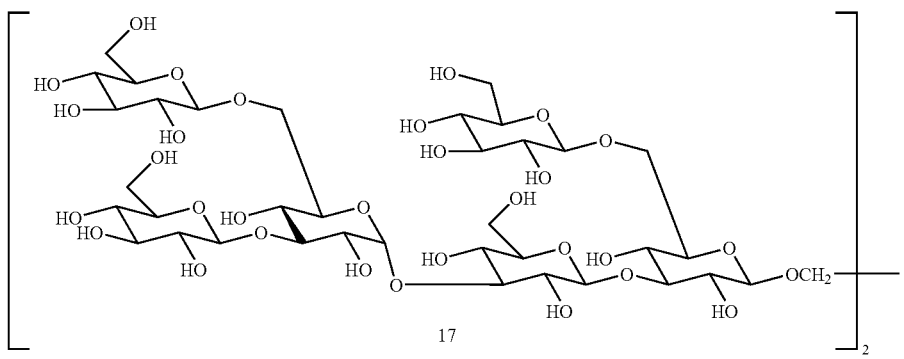

EXAMPLE 6

Preparation of Sulfated Octyl Hexaoside 25

Sulpher trioxide-pyridine complex (4 g) was dissolved in DMF (5 mL), and the solution was heated to 80° C. To this solution was added a solution of octyl glycoside 18' in pyridine (15 mL) dropwise. The mixture was stirred at 80° C. for 100 min, and the supernatant was discarded at 80° C. The viscous residue was washed with methanol three times, and the product was dissolved in water (15 mL). BaAc$_2$ was added to neutralize the mixture to pH 6. The mixture was centrifuged, the supernatant was separated, and the Ba salt precipitate was washed 3 times. The supernatant and washings were combined, and treated with Dowex 50W resin. The resin was washed with water until neutral, and the eluent was neutralized with sodium acetate, and diluted with acetone (1 L). The mixture was centrifuged generating sulfated octyl hexaoside 25 as brown powders (0.82 g, 51%). Elemental analysis: S % 12.7%, degree of sulfation 45%; $[\alpha]_D$ –14.7° (c 0.1, H$_2$O); $^{13}$C NMR (100 MHz, D$_2$O): δ 102.7, 102.4, 102.3, 102.1, 102.1, 97.2 (6 C-1), 85.7, 85.2, 85.0 (3 C-3).

EXAMPLE 7

Preparation of Sulfated Heptasaccharide 26

Sulfated heptasaccharide 26 was obtained from 24 by the same procedure as described for the preparation of 25. Elemental analysis: S % 12.3%, degree of sulfation 44%; $[\alpha]_D$ –13.2° (c 0.2, H$_2$O); $^{13}$C NMR (100 MHz, D$_2$O): δ 102.9, 102.6, 102.5, 102.2, 102.2, 101.9, 97.6 (7 C-1), 86.1, 85.8, 85.5, 85.2 (4 C-3).

EXAMPLE 8

The said Oligosaccharides, their Sulfates and Dendrimers as Medicinal Compounds Several reports have indicated that carbohydrates can not directly inhibit tumorigenesis. Thus, the inhibition of tumor cells by the said oligosaccharides was tested using implanted tumor cells in mice.

(1) Tests of the said Oligosaccharides and their Sulfates on Mice in which Tumor Cells were Implanted.

A. Materials and Methods

Cell line for the tests: U$_{14}$ cell line was procured from The Tumor Research Group, The Institute of Chinese Herbal Medicine, Chinese Academy of Traditional Chinese Medicine;

Animals for the tests: 70 Kunming male mice (weight 20±2 g, grade II) were obtained from the Experimental Animal Center, the Chinese Academy of Medicine.

Medicine for control test: Cyclophosphamide was obtained from Shanghai Hualian Pharmaceutical Ltd, permit number 012034, 1995, Shanghai.

Mice grouping and administration:

a. U$_{14}$ cell line group: physical saline, IP, 0.2 mL/d×10 d b. Group treated with hexasaccharide 18: IP 10 mg/kg×10 d, 0.2 mL/d c. Group treated with octyl hexaoside 18': IP 10 mg/kg×10 d, 0.2 mL/d d. Group treated with heptasaccharide 24: IP 10 mg/kg× 10 d, 0.2 mL/d e. Group treated with sulfated hexaose 25: IP 10 mg/kg× 10 d, 0.2 mL/d f. Group treated with cyclophosphamide: IP, 70 mg/kg×10 d, 0.1 mL/d (Cyclophosphamide was given to the mice by intraperitoneal at 24 h after the planting. After 48 h of the 1$^{st}$ injection, the 2$^{nd}$ injection was given, and after 48 h of the 2$^{nd}$ injection, the last injection was given).

Test: U$_{14}$ cells obtained from U$_{14}$ mouse were diluted and counted. Each mouse was implanted with 0.2 ml (corresponding to 4×10$^6$ cells). A total of sixty mice were implanted.

B. Test Results 1 h post administration of the last dose, the mice were weighed. The right-upper arm of the mice was cut after sterilization, and the tumor section was removed. The quotient of noumenal tumor (%) and inhibition (%) were calculated.

Inhibition of $U_{14}$ tumor by oligosaccharides (±SD)

| groups | weight (g) | quotient of noumenal tumor (%) | inhibition (%) |
|---|---|---|---|
| a. $U_{14}$ cell line group | 29.33 ± 1.65 | 4.21 ± 1.91 | |
| b. treatment with 18 | 27.40 ± 1.90 | 2.63 ± 0.90 | 29.41 |
| c. treatment with 18' | 27.45 ± 2.67 | 1.54 ± 0.56** | 58.43 |
| d. treatment with 24 | 28.85 ± 1.32 | 2.54 ± 1.89 | 41.21 |
| e. treatment with 25 | 28.10 ± 1.79 | 1.51 ± 0.41** | 61.14 |
| f. treatment with 17 | 28.10 ± 1.82 | 1.51 ± 0.43** | 61.13 |
| g. treatment with cyclophosphamide | 28.00 ± 1.78 | 1.86 ± 0.73** | 43.89 |

*Compared to $U_{14}$ cell line group,
*P <0.05
**P < 0.01

The results obtained above indicate that the said oligosaccharides can effectively inhibit $U_{14}$ cells explanted into mice. The glycoside of the said oligosaccharides with long fatty acid chains as the aglycones were more active, while sulfation of the said oligosaccharides also increases the inhibitory properties.

(2) Immune Enhancing Action of the Said Oligosaccharides, Sulfates, and Dendrimers A. Materials and Methods a. Medicine and reagents: synthetic lentinan hexaose 18, synthetic lentinan methyl α-heptaoside 24, synthetic lentinan octyl hexaoside 18', lentinan (brand: Tian Di Xin) is produced by Nanjing Zhenzhong Biotech Ltd.

b. Animals: C57 mice were provided by Animal Center, Academia Sinica, weighing 20±2 g.

c. grouping and administration: the 50 mice were randomly allocated to 10 groups according to weight

| | | | |
|---|---|---|---|
| (1) control group: physical saline | IP | 0.1 mL/d × 8d | |
| (2) treatment with hexaose 18 | IP | 1 mg/kg, 0.1 mL/d × 8d | |
| (3) treatment with methyl α-heptaoside 24 | IP | 1 mg/kg, 0.1 mL/d × 8d | |
| (4) treatment with octyl hexaoside 18' | IP | 1 mg/kg, 0.1 mL/d × 8d | |
| (5) treatment with lentinan (low dose) | IP | 1 mg/kg, 0.1 mL/d × 8d | |
| (6) control group: physical saline | IP | 0.1 mL/d × 8d | |
| (7) treatment with hexaose 18 | IP | 10 mg/kg, 0.1 mL/d × 8d | |
| (8) treatment with methyl α-heptaoside 24 | IP | 10 mg/kg, 0.1 mL/d × 8d | |
| (9) treatment with octyl hexaoside 18' | IP | 10 mg/kg, 0.1 mL/d × 8d | |
| (10) lentinan (high dose) | IP | 10 mg/kg 0.1 mL/d × 8d | |

B. The C57 Mice were used as Experiment Objects:

The mice were injected IP with different doses of lentinan oligosaccharides listed above. The injection lasted for one week. Then the spleen B lymphocytes were extracted. The following experiment was then performed with the extracted lymphocytes: the $10^6$ B cells were transferred to 96-well "U" shaped bottom plate, then the lymphocytes of Bal/bc mice were used as antigens to stimulate the B cells. After 4 days, $^3$H-Thymidine was intermingled with the system and the B cells were collected 18 hours after. The isotopic incorporation was assessed by scintillation counting. Compared with positive control and minus control, the immuno-enhanced effect of these oligosaccharides was evaluated.

C. Results

Testing results for the immune enhancing activity of lentinan oligosaccharides

| Group | $^3$H-TdR incorporation | enhancement rate (%) |
|---|---|---|
| (1) Control | 3394 | 100 |
| (2) Lentinan hexaose 18 (1 mg/kg) | 5497 | 162 |
| (3) Lentinan methyl α-heptaoside 24 (1 mg/kg) | 5546 | 163 |
| (4) Lentinan octyl hexaoside 18' (1 mg/kg) | 5547 | 163 |
| Dendrimer 17 (1 mg/kg) | 5587 | 164 |
| (5) Lentinan (1 mg/kg) | 5379 | 158 |
| (6) Control | 3045 | |
| (7) Lentinan hexaose 18 (10 mg/kg) | 6084 | 200 |
| (8) Lentinan methyl α-heptaoside 24 (10 mg/kg) | 5087 | 167 |
| (9) Lentinan octyl hexaoside 18' (10 mg/kg) | 6082 | 200 |
| Dendrimer 17 (10 mg/kg) | 6102 | 201 |
| (10) Lentinan (10 mg/kg) | 5866 | 193 |

The above results indicate that the synthetic lentinan oligosaccharides have stronger immune enhancing activity than parent lentinan.

(3) Anti-Inflammatory and Anti-Infectious Properties of Sulfated Octyl Hexaoside 25

Test method: Subcutaneous air pouches were formed on the backs of mice by injecting 5 mL of sterile air below the skin of a shaved area between the scapulae of an anaesthetized mouse. After 2 days post-injection the pouch was reinflated by the injection of 2.5 mL of air. Inflammation was induced on day 6 by injecting directly into the pouch 1.0 mL of 56 mg/mL thioglycollate or 1.0 mL of saline as a control. Approximately 17-20 h after thioglycollate injection, the animals were killed, and the cellular contents of the pouch retrieved by the injection of 2.5 mL of PBS/5% FCS. The sulfated octyl hexaoside 25 was tested for its ability to inhibit the inflammatory reaction by being injected subq. in a separate site immediately following administration of the thioglycollate. Prednisolone was used as a control anti-inflammatory drug, and was injected subq. at 25 mg/kg. The total cellular contents of each pouch were determined using a Coulter Counter and different leukocyte subpopulations were assessed by immunofluorescent flow cytometry.

The results indicate that the sulfated octyl hexaoside 25 at a dose of 1 mg/kg has similar anti-inflammatory activity as prednisolone at a dose of 25 mg/kg has. The leukocyte infiltrate in air pouch is 57±7% and 56±14% in comparison to the control.

(4) Medicinal Ingredients

Ingredient 1:

The hexasaccharide 18 or 18' (1000 mg, 5000 mg, and 10000 mg respectively) was dissolved in a solution of NaCl (1%, 1000 mL). The solutions had concentrations of 1 mg/L, 5 mg/L, and 10 mg/L, respectively, and were used as the injection medicinal. This injection medicinal was usually prepared just before use.

Ingredient 2:

Using the same method as described in ingredient 1, but the heptasaccharide with formulas 24 was used.

Ingredient 3:

Starch (99 g), glucose (99 g), and the hexasaccharide 25 (1 g) were mixed uniformly to get pills (1000), each of which weighs 200 mg containing the hexasaccharide (1 mg).

Ingredient 4:

Using the same method as described in ingredient 3, but the heptasaccharide with formulas 26 was used.

Possibility of Industrial Application

The said oligosaccharides, their sulfate derivatives and dendrimers in this invention are very effective at inhibition of $U_{14}$ tumor cells, and enhancing the immune response. The sulfated oligosaccharides have stronger tumor inhibitory activity, and they also have anti-inflammatory and anti-infectious properties. These substances can be used for the preparation of anti-tumor, anti-inflammatory and anti-infectious medicinal compounds.

The invention claimed is:

1. A glucose oligosaccharide and sulfates thereof, wherein the glucose oligosaccharide is presented by the following formula [I]:

[I]

in the formula,
[Rx]n=backbone of the said glucose oligosaccharide, Rx=glucose residue, and n=an integer of 4 to 14;
$(R_1)m$=side chain of the said glucose oligosaccharide, $R_1$=glucose monosaccharide or oligosaccharide, m=an integer of 0 to 4;
$R_2$ and $R_3$=nonreducing and reducing end respectively, $R_2$=H and $R_3$=H or $C_{1-20}$ hydrocarbon group;
the backbone of the said glucose oligosaccharides has at least one α-(1→3)-linkage, and has β-(1→3)-linkage or β-(1→4)-linkage the said side chain $R_1$ is attached to the backbone with a β-(1→6)- or α-(1→6)-linkage.

2. The glucose oligosaccharide and sulfates thereof of claim 1, wherein the said oligosaccharide has characteristic side chains $R_1$ which are closely or separately positioned.

3. The glucose oligosaccharide and sulfates thereof of claim 1, wherein the said oligosaccharides have characteristic side chains $R_1$ which are separated by one glucose residue of the backbone or by more than 2 glucose residues of the backbone.

4. The glucose oligosaccharide and sulfates thereof of claim 1, wherein the degree of hydroxyls sulfation of the said oligosaccharides is more than 0.2.

5. The glucose oligosaccharide and sulfates thereof of claim 4, wherein the degree of hydroxyls sulfation of the said oligosaccharides is 0.33 to 0.67.

6. The glucose oligosaccharide and sulfates thereof of claim 1 wherein $R_3$ is a $C_{1-18}$ hydrocarbon group.

7. The glucose oligosaccharide and sulfates thereof of claim 1, wherein the said oligosaccharide includes tetrasaccharide, pentasaccharide, hexasaccharide or heptasaccharide.

8. The glucose oligosaccharide and sulfates thereof of claim 7, wherein the said tetrasaccharide backbone includes β-Gluc-1→3-α-Gluc-1→3-β-Gluc-1→3-Gluc.

9. The glucose oligosaccharide and sulfates thereof of claim 7, wherein the said pentasaccharide backbone includes β-Gluc-1→3-α-Gluc-1→3-β-Gluc-1→3-β-Gluc-1→3-Gluc, or β-Gluc-1→3-α-Gluc-1→3-β-Gluc-1→3-α-Gluc-1→3-Gluc.

10. The glucose oligosaccharide and sulfates thereof of claim 7 wherein the said hexasaccharide includes the following formula 18, or 18'.

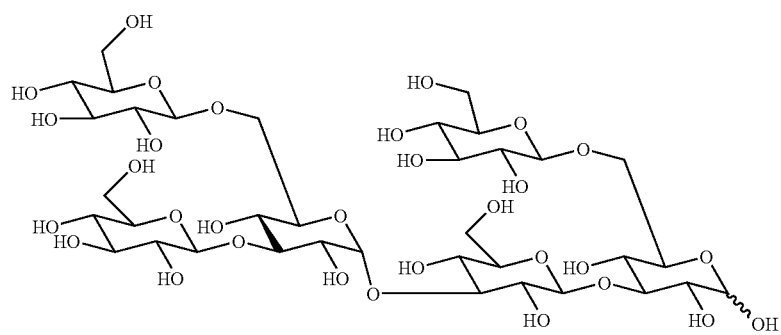

18

-continued

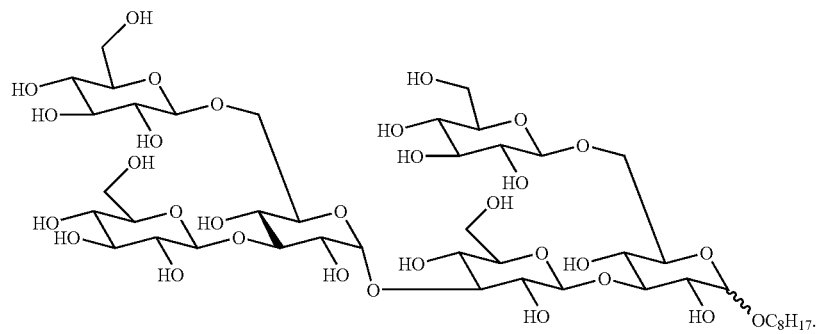

11. The glucose oligosaccharide and sulfates thereof of claim 7, wherein the said heptasaccharide includes the following formula 24:

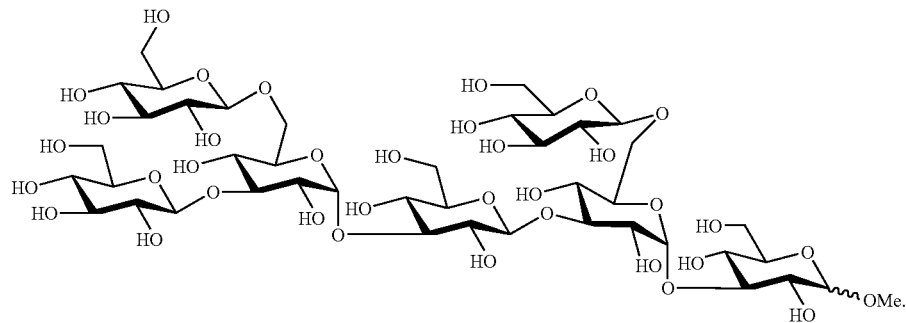

12. An antitumor, anticancer and immune enhancing medicament comprising a therapeutically effective amount of the glucose oligosaccharide and sulfates thereof of claim 1.

13. An anti-inflammatory and anti-infectious medicament comprising therapeutically effective amount of the glucose oligosaccharide and sulfates thereof of claim 1.

14. An antitumor, anticancer and immune enhancing method comprising the step of the administration of therapeutically effective amount of the glucose oligosaccharide and sulfates thereof of claim 1 to a subject in need thereof.

15. An anti-inflammatory and anti-infectious method comprising the step of the administration of therapeutically effective amount of the glucose oligosaccharide and sulfates thereof of claim 1 to a subject in need thereof.

* * * * *